United States Patent
Kline

(10) Patent No.: US 10,610,403 B2
(45) Date of Patent: Apr. 7, 2020

(54) DENTAL APPLIANCE

(71) Applicant: John C. Kline, Akron, OH (US)

(72) Inventor: John C. Kline, Akron, OH (US)

(*) Notice: Subject to any disclaimer, the term of this patent is extended or adjusted under 35 U.S.C. 154(b) by 1062 days.

(21) Appl. No.: 14/479,737

(22) Filed: Sep. 8, 2014

(65) Prior Publication Data

US 2014/0373852 A1    Dec. 25, 2014

Related U.S. Application Data

(63) Continuation-in-part of application No. 13/208,476, filed on Aug. 12, 2011, now Pat. No. 8,826,913.

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ...... A61F 2005/563; A61F 5/566; A61F 5/56; A61C 7/08; A61C 7/36; A61C 7/10; A61C 5/20; A61C 5/90
USPC ................. 128/848, 859, 861–862
See application file for complete search history.

(56) References Cited

U.S. PATENT DOCUMENTS

| | | | |
|---|---|---|---|
| 3,211,143 A * | 10/1965 | Grossberg | A63B 71/085 128/862 |
| 3,813,781 A * | 6/1974 | Forgione | A61C 9/00 433/68 |
| 4,304,227 A | 12/1981 | Samelson | |
| 4,848,365 A | 7/1989 | Guarlotti et al. | |
| 5,083,770 A | 1/1992 | Holland | |
| 5,277,202 A | 1/1994 | Hays | |
| 5,339,832 A | 8/1994 | Kittelsen et al. | |
| 5,513,656 A | 5/1996 | Boyd, Sr. | |
| 5,547,381 A | 8/1996 | Nutting | |
| 5,562,106 A | 10/1996 | Heeke et al. | |
| 5,795,150 A * | 8/1998 | Boyd | A61F 5/566 128/861 |
| 5,911,576 A * | 6/1999 | Ulrich | A61F 5/566 128/848 |
| 5,921,240 A * | 7/1999 | Gall | A61F 5/566 128/848 |
| 6,170,485 B1 * | 1/2001 | Orrico | A61F 5/566 128/848 |
| 6,263,877 B1 * | 7/2001 | Gall | A61F 5/566 128/848 |
| 6,302,686 B1 | 10/2001 | Chott et al. | |
| 6,491,521 B1 * | 12/2002 | Fowler, Jr. | A63B 71/085 128/861 |

(Continued)

*Primary Examiner* — Anna K Kinsaul
*Assistant Examiner* — Camtu T Nguyen
(74) *Attorney, Agent, or Firm* — Timothy D. Bennett; Roger D. Emerson; Emerson Thomas Bennett

(57) ABSTRACT

A dental appliance may have a pair of treatment portions and a pair of retaining surfaces that hold the treatment portions within the patient's mouth. With the treatment portions properly positioned, when the patient's mouth is in the maximum inter-cuspation position: (1) the upper canine teeth contact the upper surfaces of the treatment portions; (2) the lower teeth contact the lower surfaces of the treatment portions; and (3) no upper tooth physically contacts a lower tooth. As a result, bruxism and/or other ailments can be effectively treated.

12 Claims, 16 Drawing Sheets

(56) References Cited

U.S. PATENT DOCUMENTS

| | | | |
|---|---|---|---|
| 6,499,995 B1 * | 12/2002 | Schwartz | A61C 7/00 |
| | | | 128/862 |
| 6,830,051 B1 | 12/2004 | Lesniak et al. | |
| 7,234,467 B2 | 6/2007 | Ball | |
| 7,490,609 B2 | 2/2009 | Brown | |
| 7,556,044 B2 | 7/2009 | Ball | |
| 7,637,262 B2 | 12/2009 | Bailey | |
| 7,658,193 B2 | 2/2010 | Lesniak | |
| 7,730,891 B2 * | 6/2010 | Lamberg | A61F 5/566 |
| | | | 128/848 |
| 7,832,404 B2 | 11/2010 | Jansheski | |
| 7,882,839 B2 | 2/2011 | Ambis, Jr. | |
| 7,890,193 B2 | 2/2011 | Tingey | |
| 8,459,267 B2 | 6/2013 | Zimmerman | |
| 2003/0116164 A1 | 6/2003 | Boyd, Sr. | |
| 2013/0146067 A1 | 6/2013 | Tschackert | |
| 2014/0109919 A1 * | 4/2014 | Crout | A61F 5/56 |
| | | | 128/861 |

* cited by examiner

DENTAL APPLIANCE

This application is a continuation-in-part patent application of U.S. Pat. No. 8,826,913, filed Aug. 12, 2011, and issued Sep. 9, 2014, entitled "DENTAL APPLIANCE", the contents of which are incorporated herein by reference.

I. BACKGROUND

A. Field of Invention

This invention relates generally to methods and apparatuses related to dentistry including methods and apparatuses related to the treatment of bruxism. This invention may treat other ailments and provide other advantages as well.

B. Description of the Related Art

Bruxism is commonly known as clenching, bracing, gnashing, and or grinding of one's teeth. Stress and tension are reported as major contributors in the etiology of this condition although many theories exist as to its cause.

The problem and dispute arises as to the cause of the rampant parafunctional habits and parafunctional muscular activity found in most of the human population. The prevalence of excessively worn dentitions (including primary teeth of young children) appears to indicate that there is excessive muscular activity that is over riding any natural "cuspid protected" scheme that nature has provided. The exact cause of such muscular over activity and tension is presently unknown, however the stress of daily life seems to be a big contributor along with ingested stimulants, both natural and manmade. The muscles of mastication work in conjunction with many other head and neck muscles to provide the needed jaw movements for eating, drinking, speaking, laughing, crying, and frowning—just to mention a few. Present day occlusal guards seem to be protecting the teeth but overworking the musculature of mastication and in turn affecting many other muscles in the head and neck.

There are many known devices that are used to treat Bruxism. Essentially, the present state of the art for occlusal guards is that they provide an interface of hard plastic that the teeth (controlled by the muscles, and at night time this control is involuntary and uninhibited especially during dreaming) can "skate" around on and supposedly provide some freedom for the excessive muscular activity. The problem is that the muscle activity may actually be increased and these appliances may be triggering and enhancing muscle over activity. There seems to be a familiarity or "stomping ground" or a muscle memory "sweet spot" or "planes" that encourage more habitual and parafunctional muscle activity.

The hard interface unfortunately creates an end point or familiar home for the muscle driven teeth to teeth match-up and subsequently the recurrence of these contacts becomes more comfortable than desirable. These types of brux guards do little if anything to minimize muscle activity.

The cuspid discluding appliances utilize a hard contact for interfacing between the opposing dental arches. This contact, incline, or ramp, is used to restore, correct, manage, or create the "cuspid protected appliance" and they do just that. However there is little or no reduction of the muscle activity.

Another popular appliance known as the NTI (nociceptive trigemeinal inhibition) utilizes a hard interface between opposing dental arches in the form of an anterior deprogramming device to supposedly reduce muscle activity. It is reported to reduce parafunctional muscular activity during sleep while also disengaging ones teeth. These guards are still bulky and obtrusive and are not recommended for any wear during waking hours.

Other appliances utilizing hard interfaces use different "group function" principles to dissipate or moderate the interocclusal forces from parafunctional muscular activity during sleep. Again, none of these appliances appreciably reduce the muscular activity.

Still other appliances, some of which are soft, attempt to interface the teeth to teeth contact during the parafunctional muscular activity, however they are designed as a soft interface between all the opposing posterior teeth resulting in a mere cushioning of the parafunctional activity. This is the case in the over the counter-home remedy "boil and bite" type of mouth guard. These appliances are bulky and do not fit comfortably. The excessive opening of the vertical dimension and interference with the free-way space is damaging to the temporal mandibular joint (TMJ or jaw joint). These devices encourage excessive muscular activity much like having chewing gum in one's mouth. Covering posterior teeth, whether with soft or hard material, will incite muscular activity and place undue stress on the jaw joint.

Besides the above mentioned shortcomings practically all occlusal guards require a commercial laboratory to be involved increasing the cost to the patient. Most are typically cumbersome and difficult to wear and hence many practitioners are reluctant to "sell" their patients a relatively costly device which they may not be able to regularly wear. The resulting potential for buyer's remorse is too high for most dental practitioners to enthusiastically encourage their patient base at accept. Upon merely seeing a model of a proposed, traditional type, occlusal guard, most patients immediately tend to deny their need for such treatment knowing all well they will not be able to tolerate such a device.

Estimates indicate that more than 85% of the general adult population (potentially more if considering affected children) are experiencing signs and or symptoms of bruxism. Dental professionals can easily see and verify the damaging effects of this malady; however, the insidious nature of this condition is such that most patients are totally unaware of the problem. Daytime parafunctional habits are most often denied by patients simply because of the habitual nature of the process. Much like blinking where as one has voluntary control over eyelid closure, daytime habits of clenching go completely unnoticed. Most patients have no realization of either daytime or nighttime bruxism. Rarely does a patient report to his dental practitioner that he has been clenching during sleep, yet many signs and symptoms are apparent to the observant practitioner.

Unfortunately, it is generally very difficult to convince patients that they have a bruxism problem.

The muscle activity that creates bruxism is believed by this inventor to create and/or exacerbate other ailments as well. While the medical science of how the muscle activity and the ailments interrelate is not yet fully understood, all the following ailments (and likely others) are possibly effected by the same muscle activity that causes bruxism: tinnitus, hearing loss, esophageal constriction, Eustachian tube constriction, headaches, migraine headaches, neck aches, ear aches, halitosis and the calcification of tarter on teeth.

II. SUMMARY OF THE INVENTION

This invention is a dental appliance that treats bruxism during sleep and bruxism and other related parafunctional habits during waking hours. The daytime use of this appliance is directed towards creation of a mindfulness or awareness of any related habits as opposed to using the device as a "punching bag" for release of tension etc. The sleep time wear is designed to protect natural teeth and all dental work from the damage of the somewhat uninhibited forces of bruxism during sleep.

The dental appliance of this invention may treat other ailments as well, including: tinnitus, hearing loss, esophageal constriction, Eustachian tube constriction, headaches, migraine headaches, neck aches, ear aches, halitosis and the calcification of tarter on teeth.

Using the dental appliance of this invention may assist patients with issues including: use with a teeth whitening tray, weight loss, improved athletic performance, increased body muscle strength, improved sleep quality, and endorphin release enhancement.

This invention is a dental appliance that utilizes the natural occurring phenomenon known as "canine disclusion, or canine guidance, or cuspid protected occlusion" that has been recognized in dentistry and orthodontics practically since the beginning of these professions. Canine disclusion is a principle used for practically all orthodontic cases and practically all dental reconstruction cases. It is also the principle that a majority of all occlusal guards have utilized in the past. It is the phenomenon where the opposing canines interact to disengage and protect front and back teeth from excessive wear as the patient goes from maximum inter-cuspation (when upper and lower teeth are fully interdigitated whereas respective cusp tips of upper and lower teeth are completely seated into the respective fossae of their opposing teeth) to a lateral position (lateral or protrusive excursion) while chewing. This phenomenon allows the crushing forces of mastication to occur in the maximum intercuspation position but disengages the cuspsas lateral movements occur (similar in some respects to a cow chewing its cud in a lateral manner) which protects the human teeth from damaging lateral forces.

This appliance utilizes these principles but in a completely different manner. It may be, in some embodiments, soft and the discluding principle is a misguiding element and not a guiding one.

The nature of this invention and its presentation as a "front tooth protector" is able to overcome the inherent "refusal to accept the problem" of the traditional treatments. As patients see and realize that they could actually wear this device nightly they tend to "accept" the treatment. The most effective means of patient education appears to be a co-diagnosis whereas the patient discovers the associated tooth wear with the practitioner's help. Having noticed the apparent wear of any of the cuspids (remember nature's cuspid disclusion is working to protect the teeth but not really eliminating the muscle activity) the dental practitioner gives the patient a good sized face mirror and asks the patient to approximate the cuspids as they if they fit as a puzzle. This happens almost automatically. The patient is instructed to hold that pose and together they discuss the wear. Young and old, it is practically always evident. Most often this puzzle will be evident on all four cuspids and usually also on the patient's anterior teeth. Capturing this "puzzle picture" as a digital image serves extremely well as a motivational tool when professionals make treatment recommendations and also provides an excellent documentation of the malady.

According to some embodiments of this invention, a method of treating a patient may comprise the steps of: (A) providing the patent with a mouth comprising: (1) a lower jaw comprising lower teeth; and, (2) an upper jaw comprising upper teeth comprising: (a) a first upper canine tooth on a first side of the upper jaw; and, (b) a second upper canine tooth on a second side of the upper jaw; (B) providing a dental appliance comprising: (1) a first part comprising a first treatment portion having an upper surface and a lower surface; and, (2) a second part comprising a second treatment portion having an upper surface and a lower surface; (C) positioning the first and second treatment portions of the dental appliance within the mouth so that: (1) the first treatment portion is positioned between the first upper canine tooth and the lower teeth; and, (2) the second treatment portion is positioned between the second upper canine tooth and the lower teeth; and, (D) placing the mouth into a maximum inter-cuspation position; wherein when the mouth is in the maximum inter-cuspation position: (1) the first upper canine tooth physically contacts the upper surface of the first treatment portion; (2) at least one of the lower teeth physically contacts the lower surface of the first treatment portion; (3) the second upper canine tooth physically contacts the upper surface of the second treatment portion; (4) at least one of the lower teeth physically contacts the lower surface of the second treatment portion; and, (5) no upper tooth physically contacts a lower tooth.

According to other embodiments of this invention, a dental appliance may be used with an associated patient having a mouth comprising: (1) a lower jaw comprising lower teeth; and, (2) an upper jaw comprising upper teeth comprising: (a) a first upper canine tooth on a first side of the upper jaw; and, (b) a second upper canine tooth on a second side of the upper jaw. The dental appliance may comprise: (A) a first part comprising: (1) a first retaining surface; and, (2) a first treatment portion having: (a) an upper surface; and, (b) a lower surface separated from the upper surface by a first thickness; (B) a second part comprising: (1) a second retaining surface; and, (2) a second treatment portion having: (a) an upper surface; and, (b) a lower surface separated from the upper surface by a second thickness; (C) wherein the dental appliance is positional within the mouth into a treatment position where: (1) the first retaining surface retains the first part to the mouth with the first treatment portion positioned between the first upper canine tooth and the lower teeth; and, (2) the second retaining surface retains the second part to the mouth with the second treatment portion positioned between the second upper canine tooth and the lower teeth; and, (D) wherein as a result of the first and second thicknesses of the first and second treatment portions, when the dental appliance is in the treatment position and the mouth is in a maximum inter-cuspation position: (1) the first upper canine tooth physically contacts the upper surface of the first treatment portion; (2) at least one of the lower teeth physically contacts the lower surface of the first treatment portion; (3) the second upper canine tooth physically contacts the upper surface of the second treatment portion; (4) at least one of the lower teeth physically contacts the lower surface of the second treatment portion; and, (5) no upper tooth physically contacts a lower tooth.

According to still other embodiments of this invention, a dental appliance may be used with an associated patient having a mouth comprising: (1) a lower jaw comprising lower teeth comprising: (a) lower incisor teeth; (b) a first lower canine tooth; and, (c) a second lower canine tooth; and, (2) an upper jaw comprising upper teeth comprising: (a) a first upper canine tooth on a first side of the upper jaw; and, (b) a second upper canine tooth on a second side of the upper jaw. The dental appliance may comprise: a body comprising a front wall, a back wall, and a top connecting the front wall to the back wall, the body defining: an incisor reception zone suitable to receive the lower incisor teeth; a first canine reception zone suitable to receive the first lower canine tooth; a second canine reception zone suitable to receive the second lower canine tooth; a first treatment portion that: (1) is positioned on the top of the body; (2) has an upper surface; (3) has a lower surface separated from the upper surface by a first thickness; (4) is positional within the mouth with the lower surface in physical contact with at least one of the lower teeth and the upper surface positioned to be physically contacted by the first upper canine tooth when the mouth is in a maximum inter-cuspation position; and, a second treatment portion that: (1) is positioned on the top of the body; (2) has an upper surface; (3) has a lower surface separated from the upper surface by a second thickness; (4) is positional within the mouth with the lower surface in physical contact with at least one of the lower teeth and the upper surface positioned to be physically contacted by the second upper canine tooth when the mouth is in a maximum inter-cuspation position. Other than the first and second treatment portions, the top has a maximum thickness; and, the first thickness and the second thickness are significantly greater than the maximum thickness.

One advantage of this invention is, a dental appliance may include making a diagnosis of damaging maladies quickly and easily.

Another advantage of this invention is, a dental appliance may comprise of a co-diagnosis almost instantaneously.

Another advantage of this invention is, a dental appliance may comprise of a formulation easily designed to each specific patient and may be accomplished by entry level personnel.

Another advantage of this invention is, a dental appliance may comprise of a small appliance worn easily and extremely comfortable day or night.

Another advantage of this invention is, a dental appliance may comprise of a device easily made in the dental office, without sophisticated laboratory equipment reducing costs in a short period of time.

Still another advantage of this invention is, a dental appliance may comprise of a device easily made by entry level dental personnel.

Still another advantage of this invention is, a dental appliance may be readily accepted by patients since "puzzle picture" enlightens patient to excessive tooth wear almost instantly.

Still another advantage of this invention is, a dental appliance may comprise of a body that minimally opens the patients vertical dimension of occlusion and hence is extremely comfortable.

Still another advantage of this invention is, a dental appliance may be worn even by those wearing the CPAP machines.

Yet another advantage of this invention is, a dental appliance may be worn over any type of dental appliance including implant supported dentistry of all types.

Yet another advantage of this invention is, a dental appliance may require only the smallest, single, lower impression (capturing the essence of only the lower front eight teeth).

Yet another advantage of this invention is, a dental appliance may be worn inconspicuously during daytime.

Yet another advantage of this invention is, a dental appliance may provide potential for wear by young children and adolescents.

Yet another advantage of this invention is, a dental appliance may provide for potential for wear by some requiring anti-snore devices.

Additional benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

IV. DETAILED DESCRIPTION OF THE INVENTION

Figure 1:
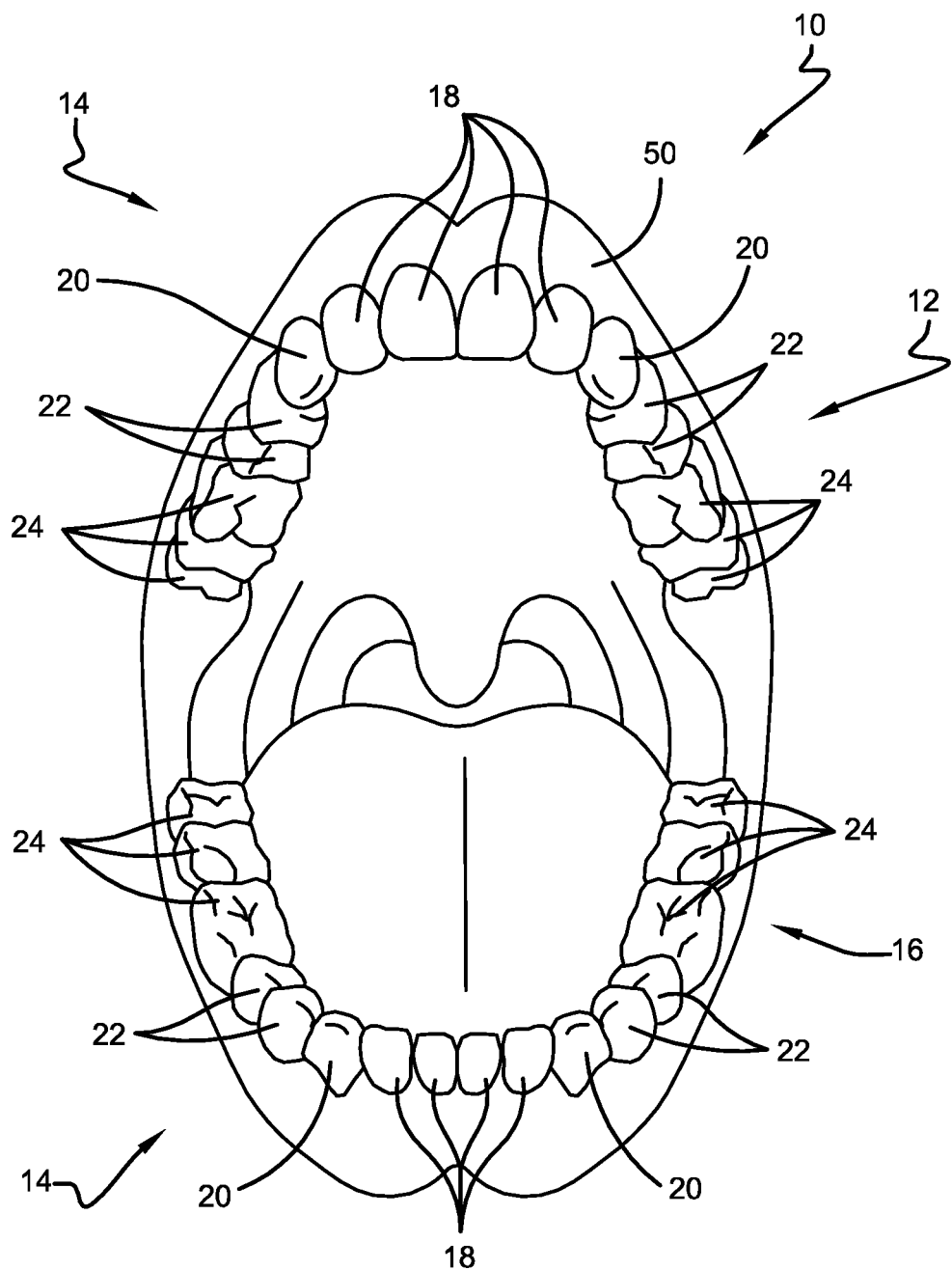
FIG. 1 is a front perspective view of a human mouth.
Figure 2:
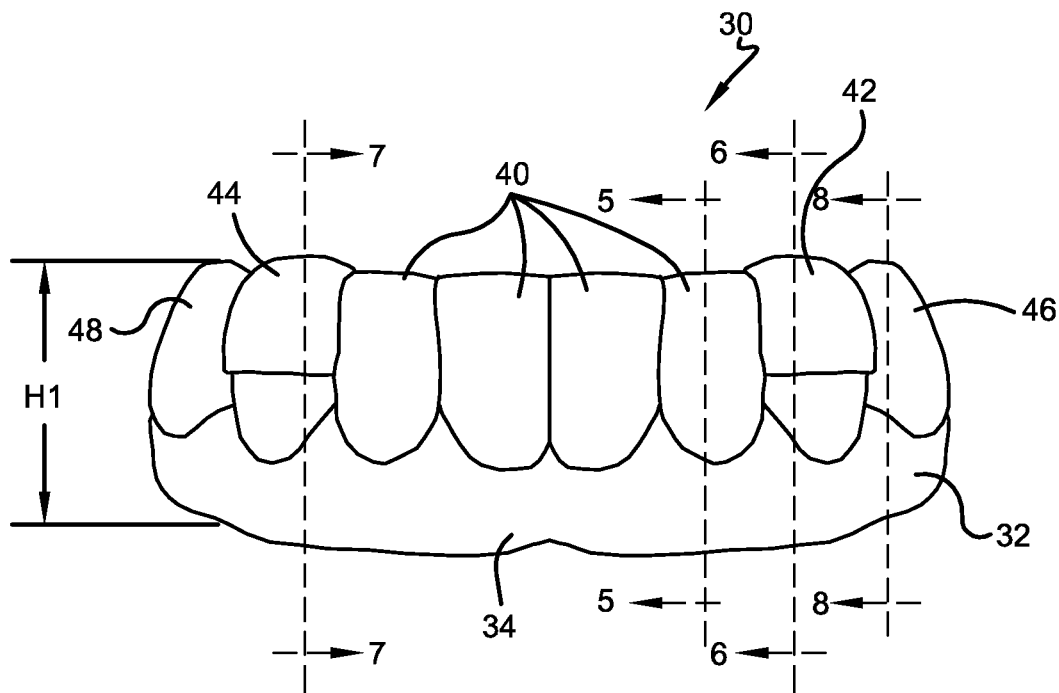
FIG. 2 is a front view of a dental appliance.
Figure 3:
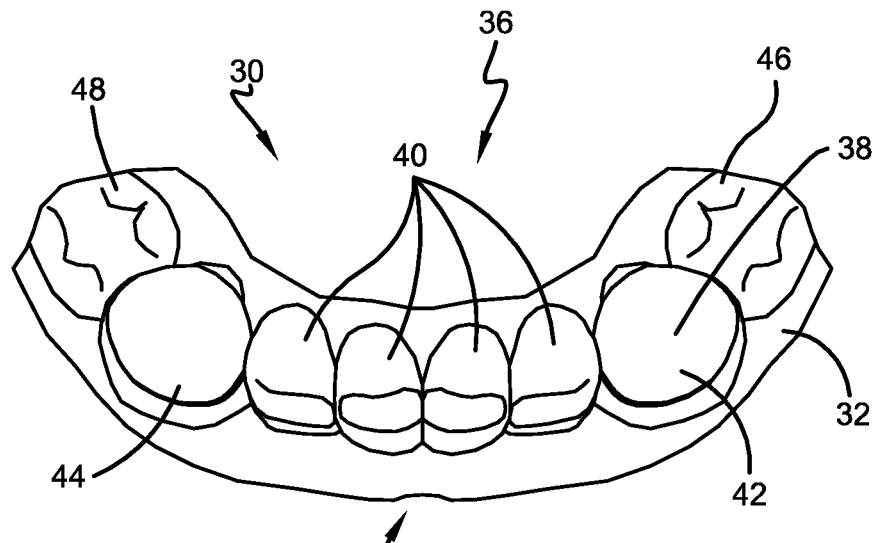
FIG. 3 is a top view of the dental appliance shown in FIG. 2.
Figure 4:
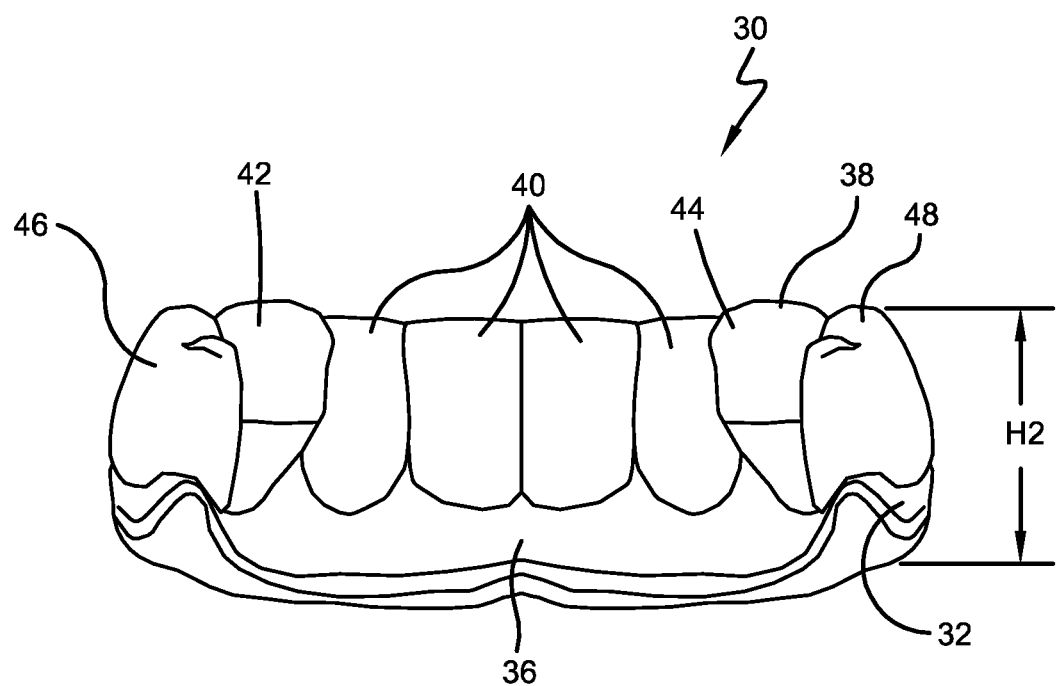
FIG. 4 is a back view of the dental appliance shown in FIG. 2.
Figure 5:
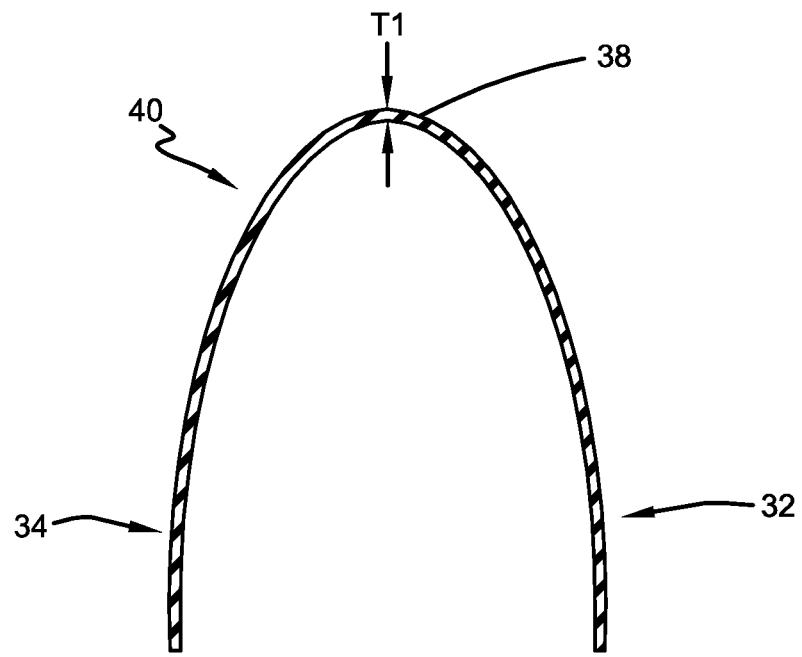
FIG. 5 is a sectional view taken through line 5-5 in FIG. 2.
Figure 6:
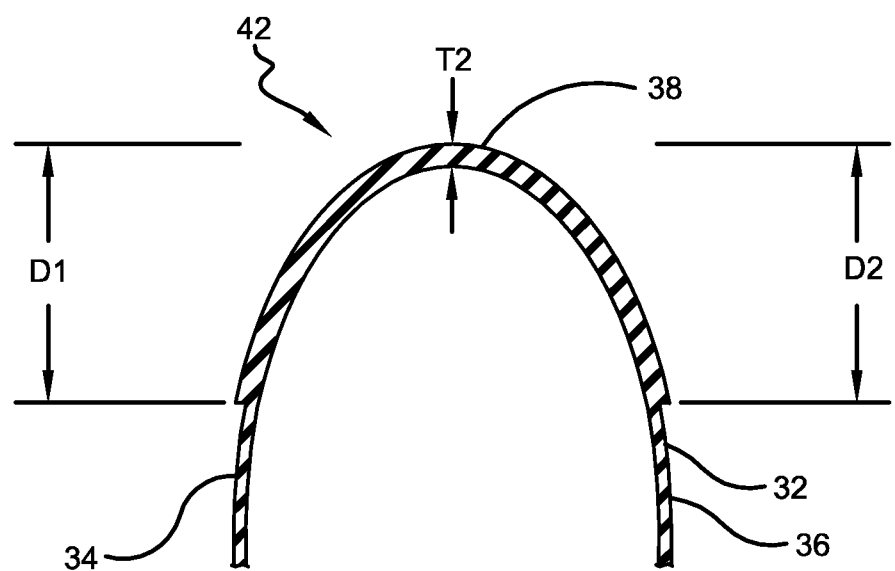
FIG. 6 is a sectional view taken through line 6-6 in FIG. 2.
Figure 7:
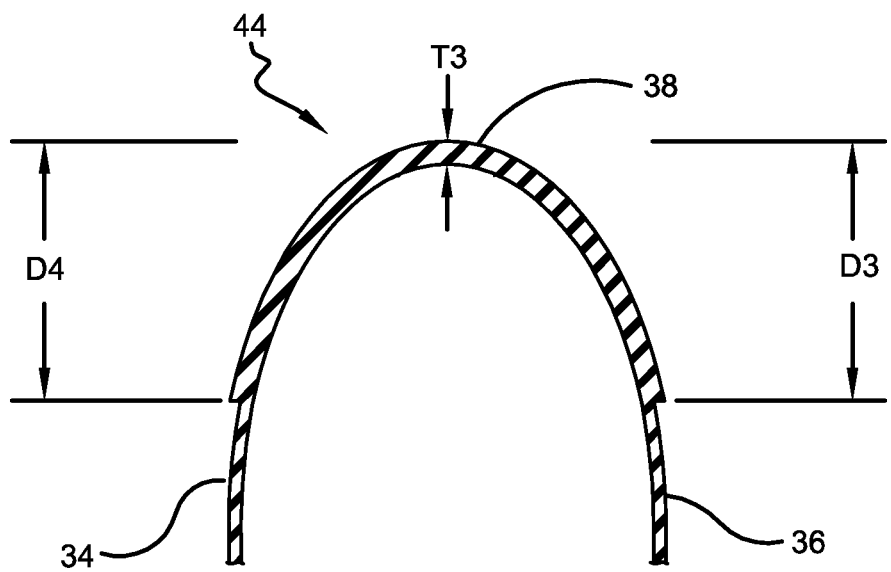
FIG. 7 is a sectional view taken through line 7-7 in FIG. 2.
Figure 8:
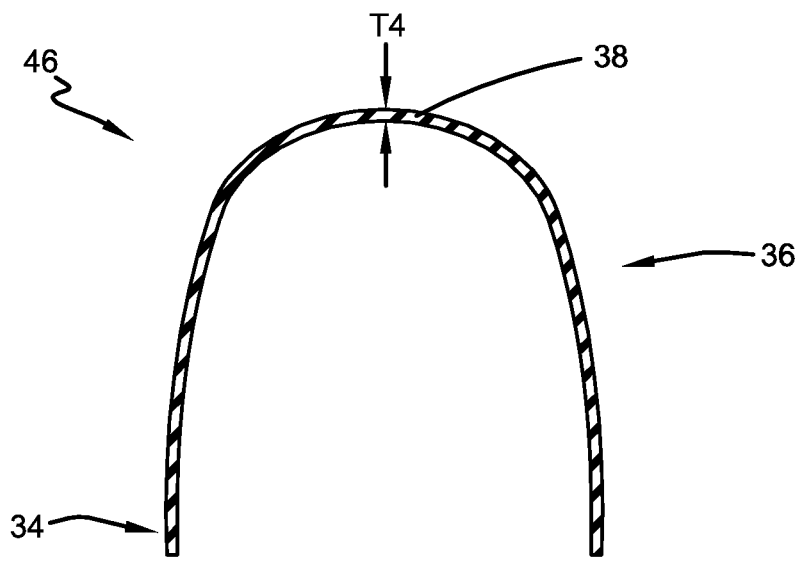
FIG. 8 is a sectional view taken through line 8-8 in FIG. 2.

Referring now to the drawings wherein the showings are for purposes of illustrating embodiments of the invention only and not for purposes of limiting the same, and wherein like reference numerals are understood to refer to like components, FIG. 1 shows a typical human mouth 10 that may use a dental appliance 30, shown in FIGS. 2-4, according to embodiments of this invention. The mouth 10 may include an upper jaw 12 having teeth 14 and a lower jaw 16 having teeth 14. More specifically, the teeth 14 for each jaw 12, 16 comprise four incisors 18, two canines (also called cuspids) 20, two premolars 22 and six molars 24. The teeth 14 may extend from dental alveolus 50 as is known to those of skill in the art.

With reference now to FIGS. 1-4, the dental appliance 30 may include one or more treatment portions, that treat bruxism and/or other ailments, and one or more retaining surfaces that retain the appliance to the patient's mouth. In one embodiment, the dental appliance 30 may include a body 32 comprising a front wall 34, a back wall 36, and a top 38 connecting the front wall 34 to the back wall 36. The body 32 may define teeth reception zones. Specifically, the body 32 may define an incisor reception zone 40 that is suitable to receive a plurality of juxtaposed incisor teeth 18, four shown, a first canine reception zone 42 suitable to receive a first canine tooth 20 that is juxtaposed to a first end of the incisor teeth 18, and a second canine reception zone 44 suitable to receive a second canine tooth 20 that is juxtaposed to a second end of the incisor teeth 18. In one embodiment, the incisor and first and second canine reception zones 40, 42, 44 define the retaining surfaces that retain or secure the dental appliance 30 to the patient's mouth. In another embodiment, additional teeth reception zones may be used as retaining surfaces. In a specific embodiment, a first premolar reception zone 46 is suitable to receive a first premolar tooth 22 that is juxtaposed to the first canine tooth 20 and a second premolar reception zone 48 is suitable to receive a second premolar tooth 22 that is juxtaposed to the second canine tooth 20 may be used.

With reference now to FIGS. 2-8, the portion of the top 38 of the body 32 that defines the incisor reception zone 40 may have a first thickness T1; the portion of the top 38 of the body 32 that defines the first canine reception zone 42 may have a second thickness T2; and, the portion of the top 38 of the body 32 that defines the second canine reception zone may have a third thickness T3. In one embodiment, the second thickness T2 and the third thickness T3 are significantly greater than the first thickness T1. In this way, the canine reception zones 42, 44 extend vertically higher than the remaining portions of the dental appliance 30 and only the canine reception zones 42, 44 are used to slightly open the vertical dimension of maximum intercuspation. These top portions of greater thickness are thus treatment portions that treat the bruxism and/or other ailment. In one embodiment, the first thickness T1 is between 0.25 millimeters and 0.75 millimeters inclusively and the second and third thicknesses T2, T3 are between 0.75 millimeters and 1.5 millimeters inclusively. In one embodiment the second and third thicknesses T2, T3 are substantially the same. The portions of the top 38 of the body 32 that define the first and second premolar reception zones 46, 48 may each have a fourth thickness T4. The fourth thickness T4 may be significantly less than the second and third thicknesses T2 and T3. In one embodiment, the fourth thickness T4 is between 0.25 millimeters and 0.75 millimeters inclusively. In one embodiment the first thickness T1 and the fourth thickness T4 are substantially the same. In one embodiment, the entire dental appliance 30 has the first thickness T1 (thus T4 equals T1) except the second and third thicknesses T2, T3.

With reference now to FIGS. 1-4, the dental appliance 30 may be formed of any material and in any manner chosen with the sound judgment of a person of skill in the art. In one embodiment, the portions of the top 38 of the body 32 that define the first and second canine reception zones 42, 44 are elastic. In this way, when opposing canines 20, 20 (one from the upper jaw 12 and the other from the lower jaw 16) contact each other, the impact may be a soft "no end point" relationship. The effect is one of a disconcerting effect on muscle habits in the patient. This is opposed to known hard surface (non-elastic) occlusal guards which permit the patient's musculature to become continuously familiar with the occlusal guard surface interface and do nothing more than interface between opposing teeth. When the canine reception zones 42, 44 are elastic, however, the muscle memory is interrupted and bruxism activity is subdued. In one embodiment, the canine reception zones 42, 44 are formed of a relatively soft plastic. In one specific embodiment, the canine reception zones 42, 44 are formed of ethylene vinyl acetate (EVA). In yet another embodiment, the entire dental appliance 30 is formed of EVA.

With reference now to FIGS. 1-8, in one embodiment, the dental appliance 30 is fitted to the teeth 14 of the upper jaw 12. In another embodiment, the dental appliance 30 is fitted to the teeth 14 of the lower jaw 16. Fitting the dental appliance 30 to the teeth 14 of the lower jaw 16 has the advantage of using gravity to help maintain the dental appliance 30 in place. Another advantage of fitting the dental appliance 30 to the teeth 14 of the lower jaw 16 is that the proprioception of the lower jaw 16 canines 20 differ from that of the upper jaw 12 canines 20—primarily because of the mobile nature of the mandible relative to the stationary position of the maxilla. The front wall 34 of the dental appliance 30 may have a height H1 and the back wall 36 may have a height H2. In one embodiment, the heights H1, H2 are sufficient to cover the teeth 14 but no more. In another embodiment, shown, the heights H1, H2 are sufficient to cover the teeth 14 and to at least partially cover the dental alveolus 50 from which the teeth 14 extend (this can be seen by observing the portion of the dental appliance 30 that extends below the various tooth reception zones 40, 42, 44, 46, 48). The portions of the first and second canine reception zones 42, 44 that have the second and third thickness T2, T3, respectively, may be sized and shaped in any manner chosen with the sound judgment of a person of skill in the art. In one embodiment, the portion of the first canine reception zone 42 that has the second thickness T2 may extend, as shown, entirely across the width W1 of the first canine reception zone 42 and a distance D1 of at least 3.0 millimeters down the front wall 34 and a distance D2 of at least 3.0 millimeters down the back wall 36. Similarly, the portion of the second canine reception zone 44 that has the third thickness T3 may extend, as shown, entirely across the width W2 of the second canine reception zone 44 and a distance D3 of at least 3.0 millimeters down the front wall 34 and a distance D4 of at least 3.0 millimeters down the back wall 36. In another embodiment, the distances D1, D2, D3 and D4 are about 5.0 millimeters.

With reference now to FIGS. 2-3 and 10-12, in another embodiment a dental appliance 60 that may be used to treat bruxism and/or other ailments may be similar to the previously described dental appliance 30. However, for this embodiment a middle portion of the front wall 34 is removed. In this way, one or more of the incisor teeth 18 (four shown) are not covered by the dental appliance 60 and thus may be visible even when the dental appliance 60 is being worn. This may make it easier for the patient to wear the dental appliance 60 during the day. In yet another embodiment, not shown, a middle portion of the back wall 36 is removed.

With reference now to FIGS. 2-3 and 13-14, in yet another embodiment a dental appliance 70 that may be used to treat bruxism and/or other ailments may be similar to the previously described dental appliance 30. However, for this embodiment the dental appliance 70 has two separate parts or sections 72, 74. For the specific embodiment shown, each section 72, 74 covers one canine 20 and one neighboring premolar 22. In another specific embodiment, now shown, each section 72, 74 covers one canine 20 and one neighboring incisor 18. In yet another specific embodiment, not shown, each section 72, 74 covers one canine 20, one neighboring premolar 22, and one neighboring incisor 18 (three teeth total). In still another specific embodiment, not shown, each section 72, 74 covers only one canine 20.

Figure 9:
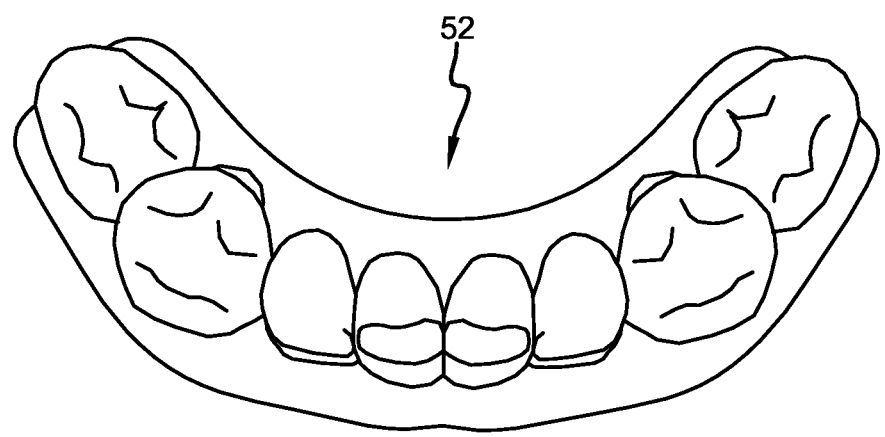
FIG. 9 is a top view of a model.
Figure 10:
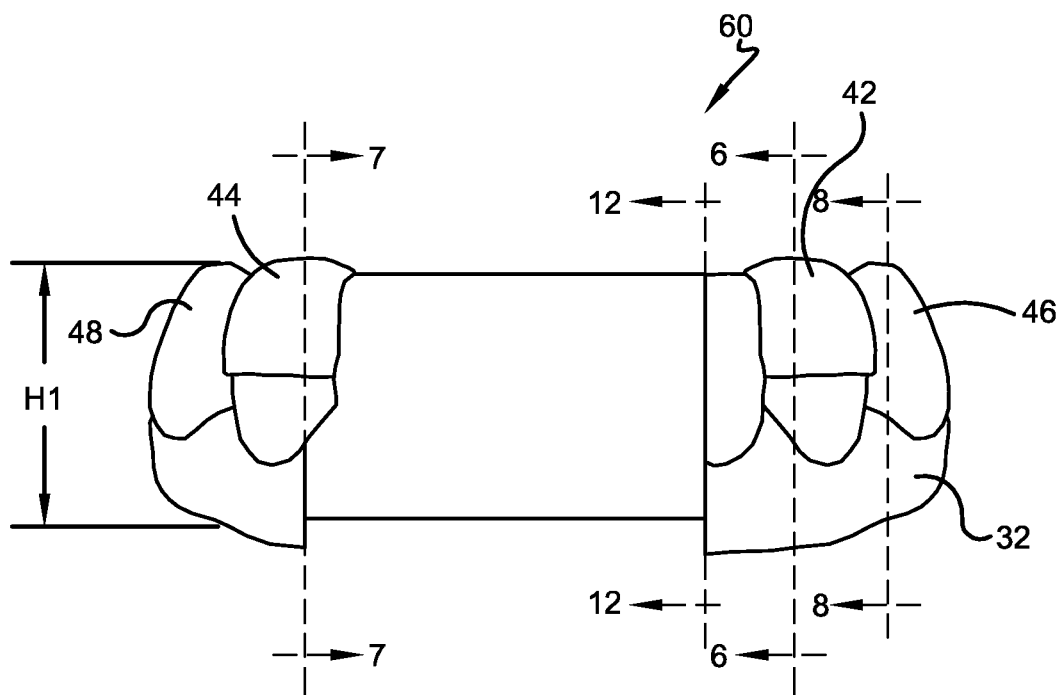
FIG. 10 is a front view of a dental appliance according to another embodiment.
Figure 11:
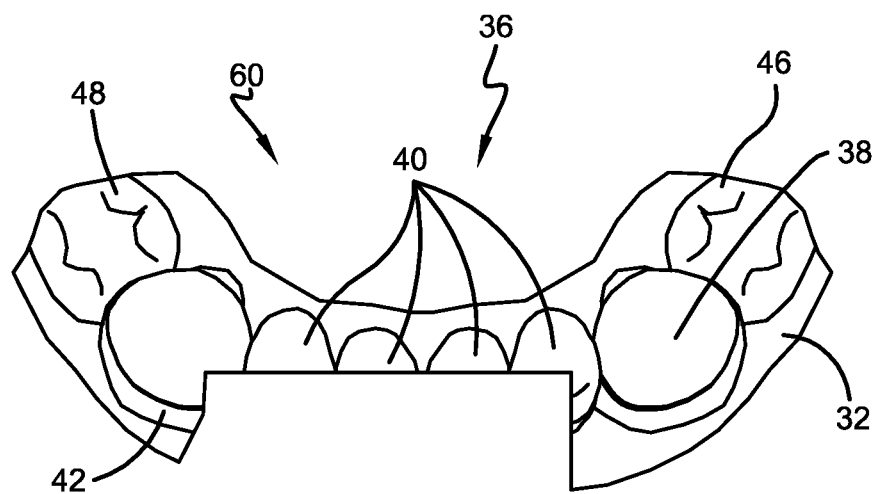
FIG. 11 is a top view of the dental appliance shown in FIG. 10.
Figure 12:
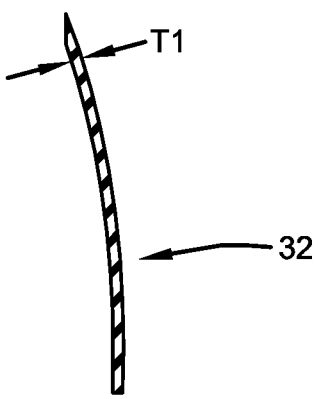
FIG. 12 is a sectional view taken through line 12-12 in FIG. 10.
Figure 13:
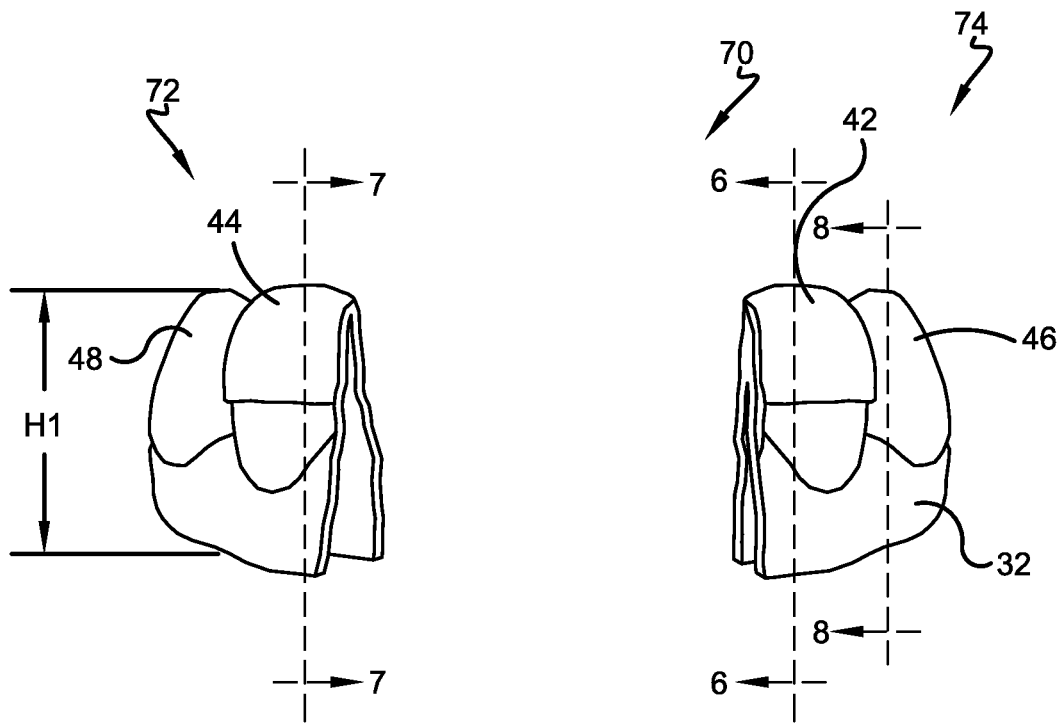
FIG. 13 is a front view of a dental appliance according to yet another embodiment.
Figure 14:
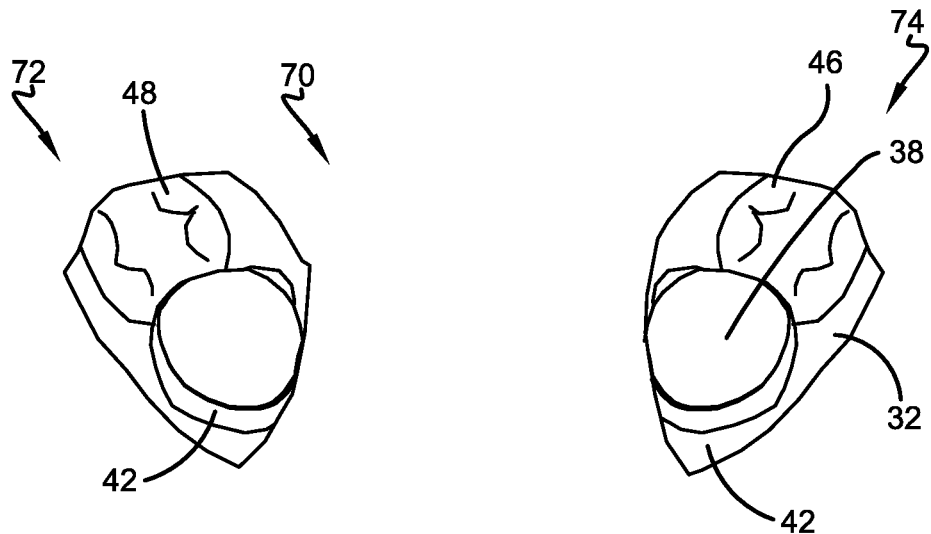
FIG. 14 is a top view of the dental appliance shown in FIG. 13.

With reference now to all the FIGURES, the fabrication and use of the dental appliance 30, 60, 70 according to some embodiments will now be described. First, it may be determined that the patient has bruxism. This determination may, of course, be made by a dental practitioner. However, a co-diagnoses (with the patient) is beneficial as the patient is then more likely to accept the required treatment. In one specific embodiment, a reflective surface such as a mirror may be used to show the patient the wear status of the patient's teeth. The most obvious worn enamel (usually on one or more front teeth) is easily seen by the patient forming a "puzzle picture" for the patient. This wear status may be shown to the patient on a monitor and a picture may be taken of the wear status, such as by a digital camera. The patient may then be shown an example dental appliance to allay any fears of wearing the dental appliance 30, 60, 70. The dental practitioner may also explain the benefits of using the dental appliance 30, 60, 70 including muscle relaxation verses muscle tension, daytime mindfulness exercises using the dental appliance 30, 60, 70, reduction in cracked teeth and the fact that all dental work will last longer when protected from the forces of bruxism. Once the patient decides that the dental appliance 30, 60, 70 will be beneficial, the dental practitioner can then fabricate it. To do this, the dental practitioner may first determine the required thicknesses for the dental appliance 30, 60, 70 using the puzzle picture. Next, the dental practitioner may make a relatively small impression of the anterior quadrant of the patient's teeth with an alginate material. A model, such as model 52 shown in FIG. 9, is then made from the impression. The dental appliance 30, 60, 70 may then be vacuum formed, trimmed, and then delivered to the patient, custom made, immediately. It can be formed of any thickness and in any color or combination of colors chosen with the sound judgment of a person of skill in the art.

With continuing reference to all the FIGURES, once the dental appliance 30, 60, 70 is made and delivered, the patient then wears it. The dental appliance 30, 60, 70 is retained or held in place via a hydro-seal, similar to how dentures remain in place. The patient may wear the dental appliance 30, 60, 70 during sleep time to protect the patient from damage caused by bruxism or other ailments. The patient may also wear the dental appliance 30, 60, 70 during wake time to create awareness in the patient of any bruxism related habits. Applicant has discovered that for many patients, wearing the dental appliance 30, 60, 70 at night may be more important than wearing it during sleep time. As noted above, wearing the dental appliance 30, 60, 70 will disconcert muscle memory in the patient and thus will help train the patient's muscles not to grind and the like. Wearing the dental appliance 30, 60, 70 will help in providing relief for the patient from: head, neck, and shoulder muscular tension and the potentially associated sleep apnea, headaches, migraine triggers, neckaches, and shoulder aches. Applicant has discovered that for some patients wearing the dental appliance 30, 60, 70 works effectively in reducing or eliminating snoring. Wearing the dental appliance 30, 60, 70 will also help minimize dental pain, tooth thermal and tactile sensitivity, enamel abfractions and abrasions. These signs and symptoms can be treated during the day when they arise from conscious, habitual, parafunctional clenching, grinding, gnashing and bracing of one's teeth. In this case, the dental appliance 30, 60, 70 provides mindfulness for the patient which is a therapeutic approach to help attenuate the daytime tension and conscious clenching. The same signs and symptoms can also be treated at night when they arise from similar but unconscious activities. Wearing the dental appliance 30, 60, 70 also may protect the patient's teeth from germs and the like thereby protecting the teeth from tooth decay.

The dental appliances described above work well for many patients, but when retained to the lower jaw, not all patients. To achieve the best treatment, the treatment portions of the dental appliance are positioned between the patient's upper canine teeth and the patient's lower teeth when the patient's mouth is in the maximum inter-cuspation position. For some patients the upper canine teeth are not directly above the lower canine teeth when the patient's mouth is in the maximum inter-cuspation position. For these patients, if the dental appliance is retained to the lower jaw, positioning the treatment portions only over the lower canine teeth (for example, on the top of the canine reception zones) may not provide sufficient treatment area for the upper canine teeth.

Figure 15:
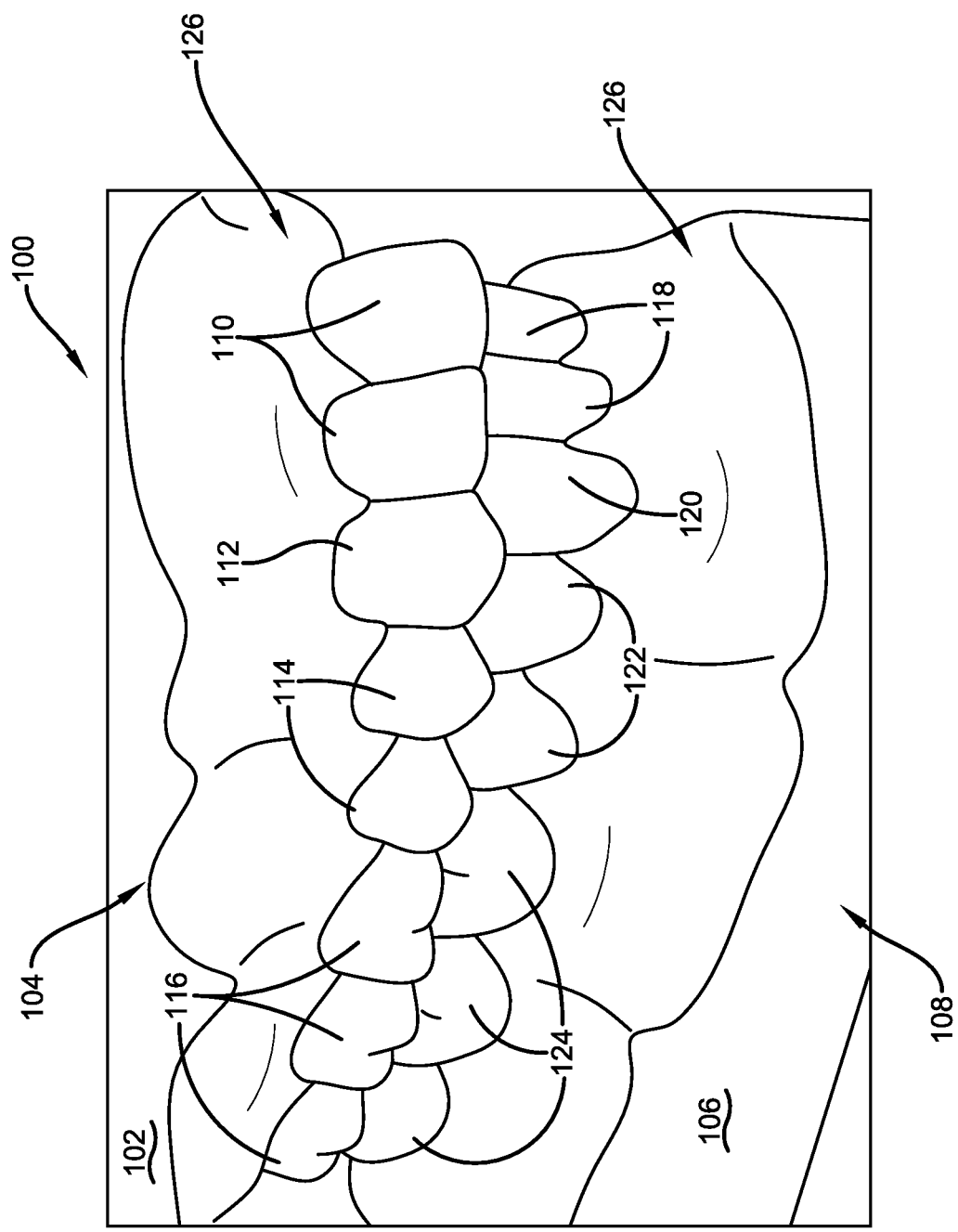
FIG. 15 is a front perspective view of a human mouth.

FIG. 15 illustrates, as a non-limiting example, the problem discussed in the previous paragraph. Human mouth 100 may include an upper jaw 102 having upper teeth 104 and a lower jaw 106 having lower teeth 108. More specifically, the upper teeth 104 may comprise upper incisors 110, upper canine 112, upper premolars 114 and upper molars 116. Similarly, the lower teeth 108 may comprise lower incisors 118, a lower canine 120, lower premolars 122 and lower molars 124. While only the right side of the mouth 100 is shown, the left side may have a similar layout of teeth—including an upper canine and a lower canine. The teeth 104, 108 may extend from dental alveolus 126 as is known to those of skill in the art. Note that the upper canine tooth 112 is not directly above the lower canine tooth 120. For this particular example, as seen better in FIG. 16, there is a offset distance D5 between an upper canine axis 128 and a lower canine axis 130, where each axis 128, 130 is perpendicular to a ground surface and passes through the corresponding canine tooth tip. The offset distance D5 will vary from patient to patient (and may occur on the opposite side; that is, the lower canine might be positioned to the left of the top canine instead of the right as shown) but whenever the offset distance D5 is significant, positioning the treatment portions only over the lower canine teeth (such as over lower canine tooth 120) will provide insufficient treatment area for the upper canine teeth (such as upper canine tooth 112). So for the embodiments now to be described, the treatment portions of the dental appliance are positioned based on the location of the patient's upper canine teeth—regardless of the position of the patient's lower canine teeth; in fact, regardless of the position of any of the patient's lower teeth.

Figure 17:
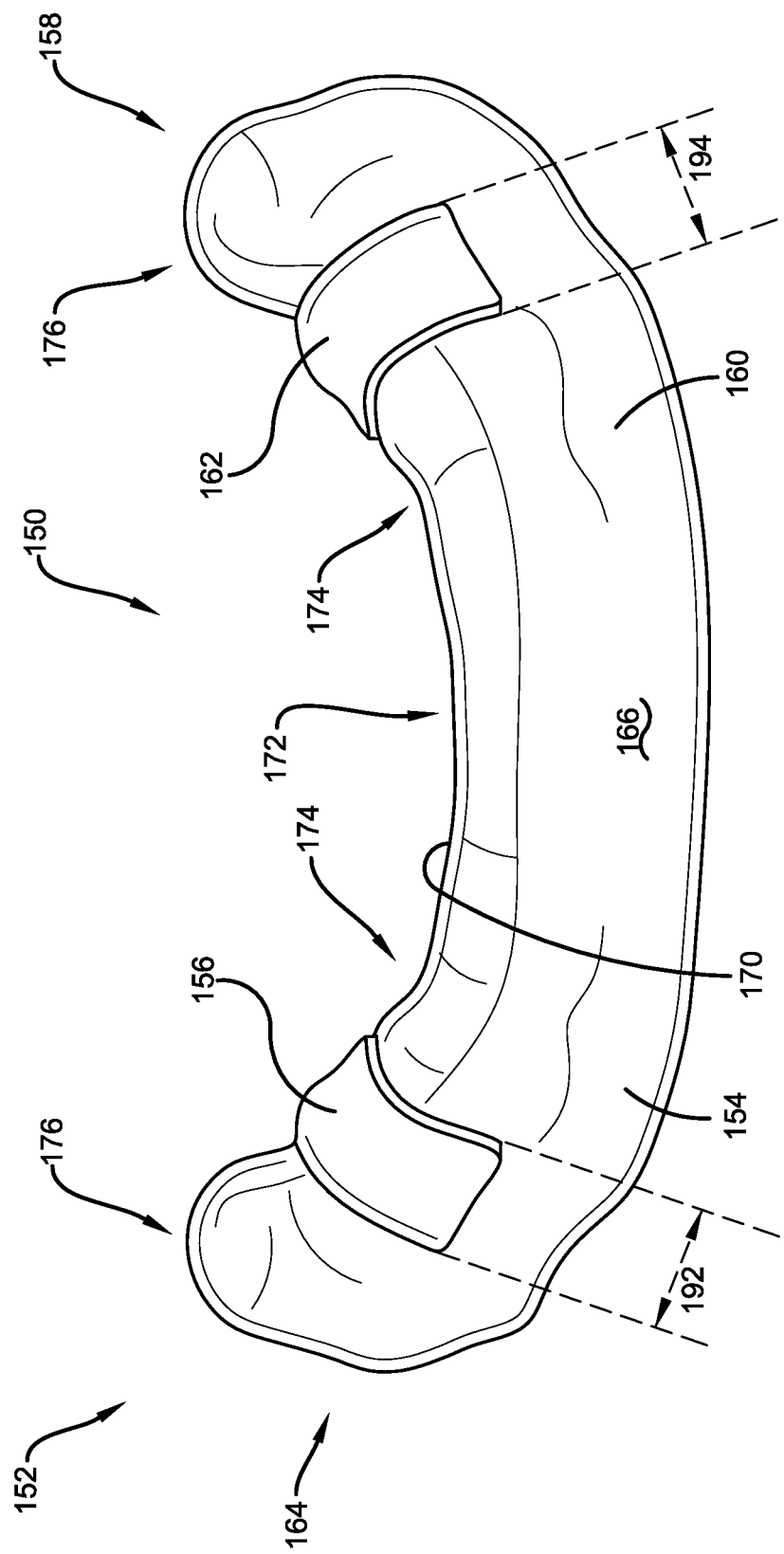
FIG. 17 is a front perspective view of a dental appliance.
Figure 18:
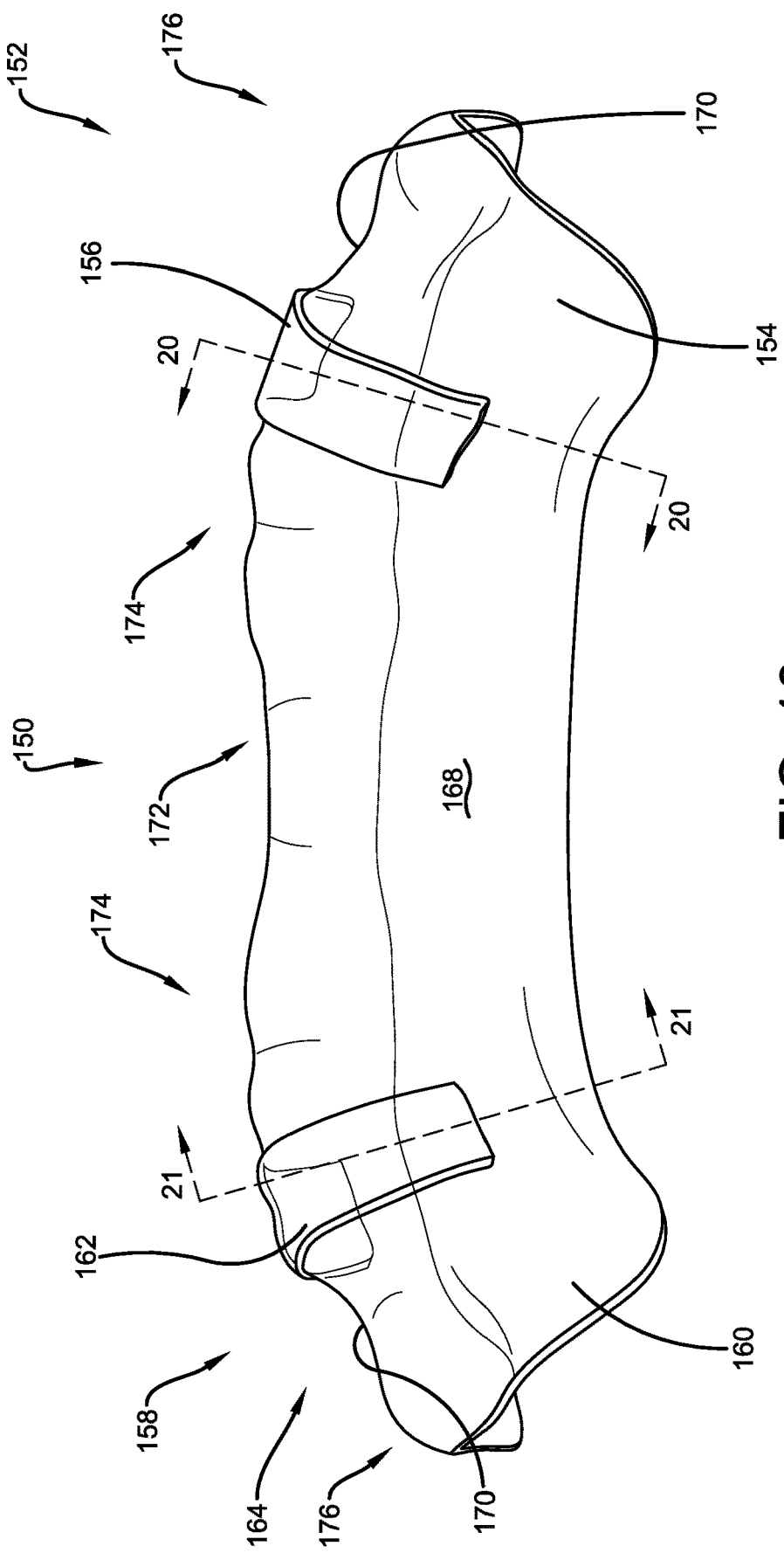
FIG. 18 is a back perspective view of the dental appliance shown in FIG. 17.
Figure 19:
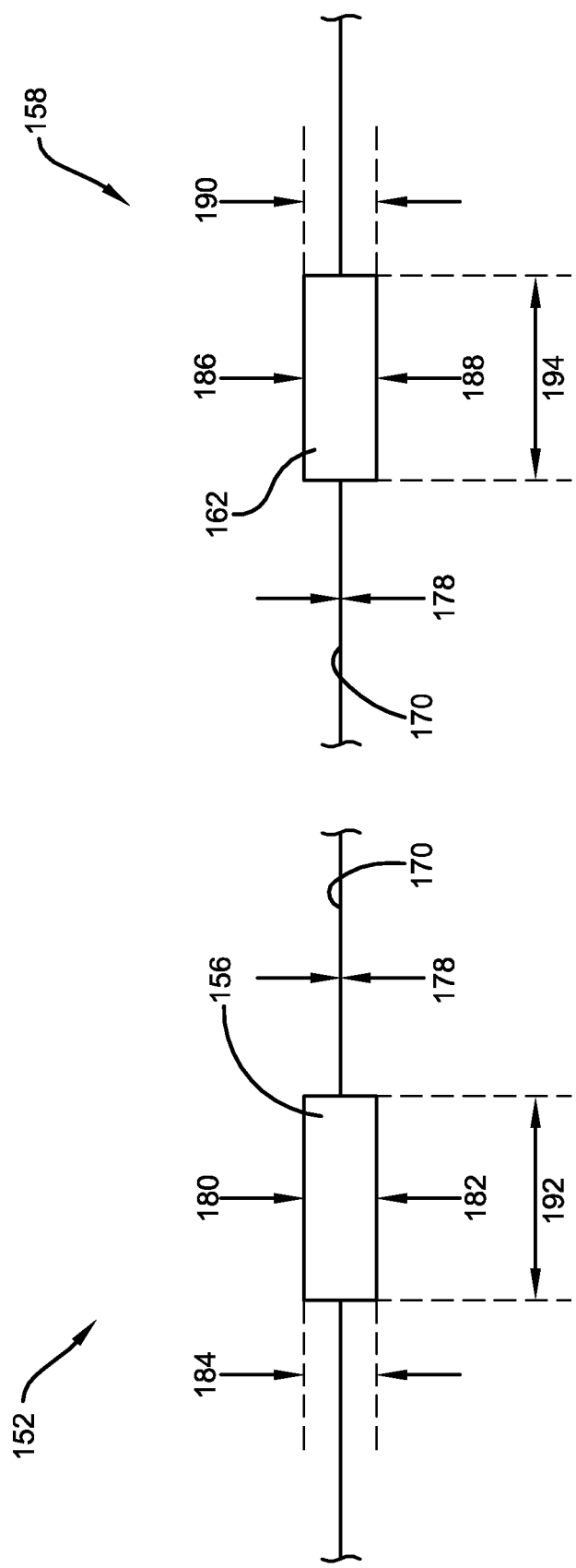
FIG. 19 illustrates sectional views of the treatment portions and tops of a dental appliance.

With reference now to FIGS. 17-18, a dental appliance 150 according to some embodiments of this invention is shown. The dental appliance 150 may include a first part 152 having a retaining surface 154 that retains the first part 152 to the patient's mouth and a treatment portion 156 positioned to engage the patient's upper canine tooth on one side of the patient's mouth. The dental appliance 150 may include a second part 158 having a retaining surface 160 that retains the second part 158 to the patient's mouth and a treatment portion 162 positioned to engage the patient's upper canine tooth on the other side of the patient's mouth.

By "engage" it is meant that the treatment portion is positioned between the patient's corresponding upper canine and the patient's corresponding lower teeth when the patient's mount is in a maximum inter-cuspation position.

With continuing reference to FIGS. 17-18, the particular retaining surfaces 154, 156 used can be any chosen with the sound judgment of a person of skill in the art that retain the corresponding parts 152, 158 within the patient's mouth with the treatment portions 156, 162 positioned to engage the patient's upper canine teeth. In one embodiment, the retaining surfaces 154, 156 are defined by a body 164 having a front wall 166, a back wall 168 and a top 170 that connects the front wall 166 to the back wall 168. Note that for dental appliances having a top, the top 170 is the only portion of the body 164 that is positioned between the patient's upper and lower teeth when the patient's mouth is in a maximum inter-cuspation position. The body 164 may include zones to receive the patient's teeth to retain the dental device to the patient's mouth as described above. For the embodiments shown in FIGS. 17-18, the body 164 has an incisor reception zone 172 suitable to receive at least one of the patient's lower incisor teeth, at least one canine reception zone 174 (two shown) suitable to receive at least one of the patient's lower canine teeth and at least one premolar reception zone 176 (two shown) suitable to receive at least one of the patient's lower premolar teeth. In another embodiment, not shown, the body 164 comprises a molar reception zone suitable to receive at least one of the patient's lower molar teeth.

Figure 20:
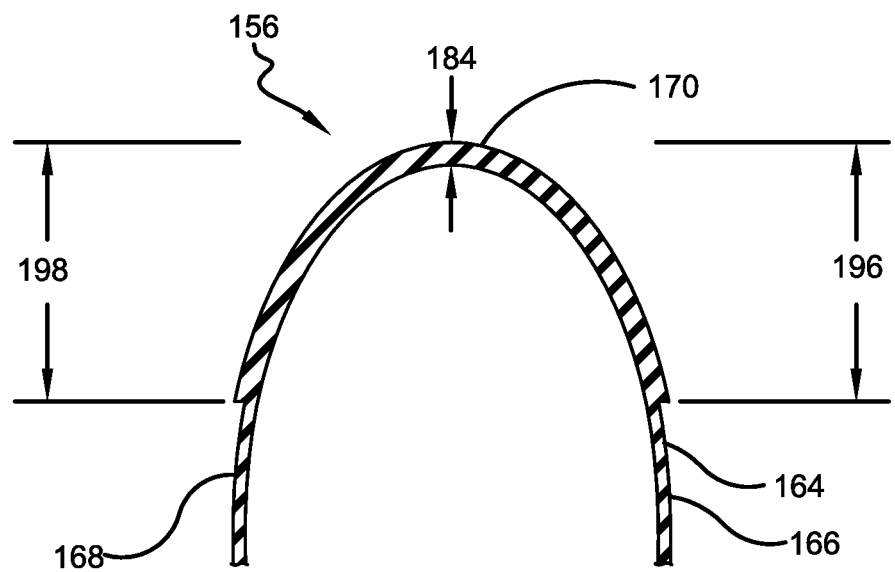
FIG. 20 is a sectional view taken through line 20-20 in FIG. 18.
Figure 21:
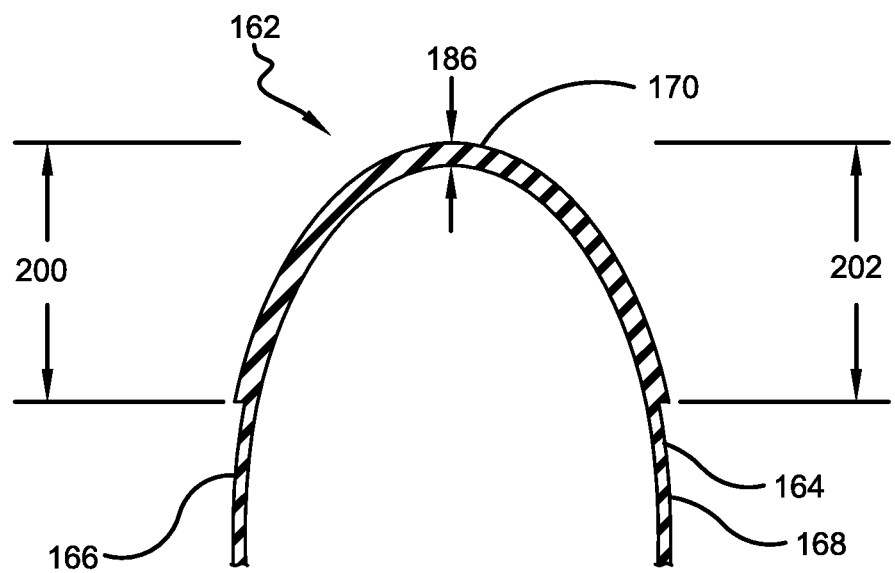
FIG. 21 is a sectional view taken through line 21-21 in FIG. 18.

With reference now to FIGS. 17-21, the treatment portion 156 may have an upper surface 180 and a lower surface 182 separated from the upper surface by a thickness 184. Similarly, the treatment portion 162 may have an upper surface 186 and a lower surface 188 separated from the upper surface by a thickness 190. For dental appliances having a top, the treatment portions 156, 162 form a part of the top. Other than the treatment portions 156, 162, the top 170 may have a maximum thickness 178. The specific dimensions of thicknesses 184 and 190 may be any chosen with the sound judgment of a person of skill in the art as long as they are significantly greater than maximum thickness 178. In one embodiment, thicknesses 184, 190 are between 0.75 millimeters and 1.5 millimeters inclusively and maximum thickness 178 is between 0.25 millimeters and 0.75 millimeters inclusively. In one embodiment the thicknesses 184, 190 are substantially the same. The treatment portions 156, 162 may have widths 192, 194 sufficient to engage with the patient's upper canine teeth as chosen by a person of skill in the art. In one embodiment, the widths 192, 194 are between 3.0 millimeters and 10.0 millimeters inclusively. In one embodiment, the widths 192, 194 are substantially the same. In one specific embodiment, the widths 192, 194 are each about 5.0 millimeters. In one embodiment, one or both of treatment portions 156, 162 do not extend down the front or back walls 166, 168 at all. In another embodiment, the treatment portions 156, 162 may extend down one or both of the walls 166, 168. FIG. 20 shows embodiments where the treatment portion 156 extends down the front wall 166 a distance 196 and extends down the back wall 168 a distance 198. FIG. 21 shows embodiments where the treatment portion 162 extends down the front wall 166 a distance 200 and extends down the back wall 168 a distance 202. The distances 196, 198, 200 and 202 may range from 0 millimeters to about 10.0 millimeters. In one embodiment, the distances 196, 198, 200 and 202 may be substantially the same. In one specific embodiment, the distances 196, 198, 200 and 202 are each about 5.0 millimeters.

Figure 22:
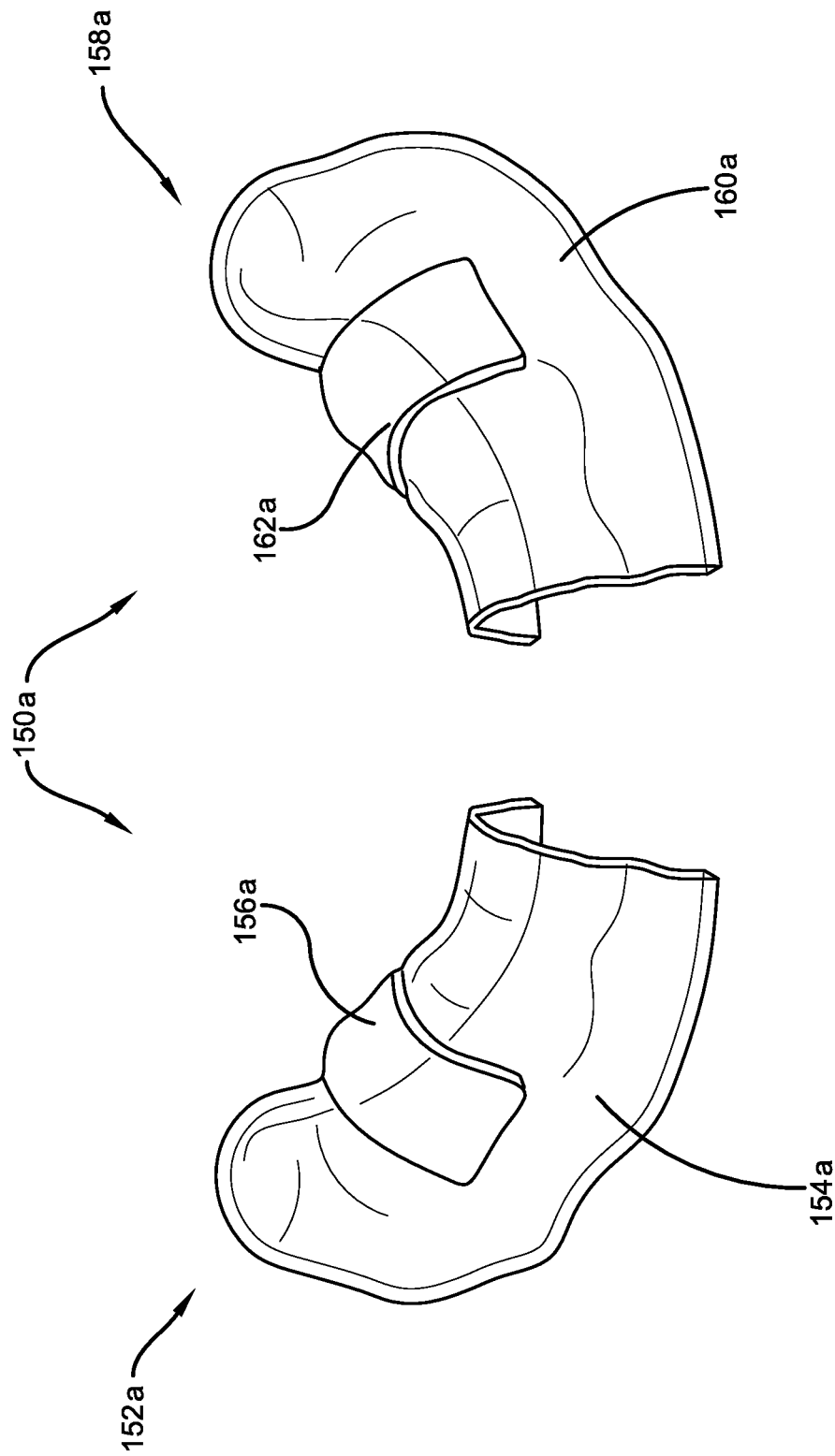
FIG. 22 is a front perspective view of a dental appliance.

For the embodiments shown in FIGS. 17-18, the first and second parts 152, 158 are connected. In one specific embodiment, the first and second parts 152, 158 are made together as a single piece. FIG. 22 shows another embodiment where dental appliance 150a may have first and second parts 152a, 158a that are not connected but are separate pieces received on opposite sides of the patient's mouth. Each part 152a, 158a may have a corresponding treatment portion 156a, 162a and retaining surface 154a, 160a. The treatment portions 156a, 162a may be sized and shaped as treatment portions 156, 162 described above. The retaining surfaces 154a, 160a may, in some embodiments, include reception zones that receive teeth, as described above. The dental appliances 150, 150a may be formed in any manner chosen with the sound judgment of a person of skill in the art, including the materials and methods described throughout this patent.

With reference now to FIGS. 17-18 and 22, the use of dental appliances 150, 150a is similar to the use of the dental appliances discussed above. The treatment portions 156, 162, 156a, 162a are positioned within the patient's mouth so that the treatment portions 156 or 156a are positioned between the upper canine tooth and the lower teeth on one side of the patient's mouth and the treatment portions 162 or 162a are positioned between the upper canine tooth and the lower teeth on the other side of the patient's mouth. The treatment portions are positioned so that when the patient's mouth is in the maximum inter-cuspation position: (1) the upper canine tooth on one side of the patient's mouth physically contacts the upper surface of one (the first) treatment portion; (2) at least one of the patient's lower teeth physically contacts the lower surface of the first treatment portion; (3) the upper canine tooth on the other side of the patient's mouth physically contacts the upper surface of the other (the second) treatment portion; (4) at least one of the patient's lower teeth physically contacts the lower surface of the second treatment portion; and, (5) no upper tooth physically contacts a lower tooth. The result is that the contact of the patient's upper canine teeth with the thicker treatment portions (when the patient's mouth is in the maximum inter-cuspation position) controls the interaction of the upper teeth with the lower teeth—thereby treating the patient. This invention also works well if the patient is wearing another dental appliance in addition to the inventive dental appliance—as long as the contact of the patient's upper canine teeth with the thicker treatment portions (when the patient's mouth is in the maximum inter-cuspation position) controls the interaction of the upper teeth with the lower teeth.

Figure 16:
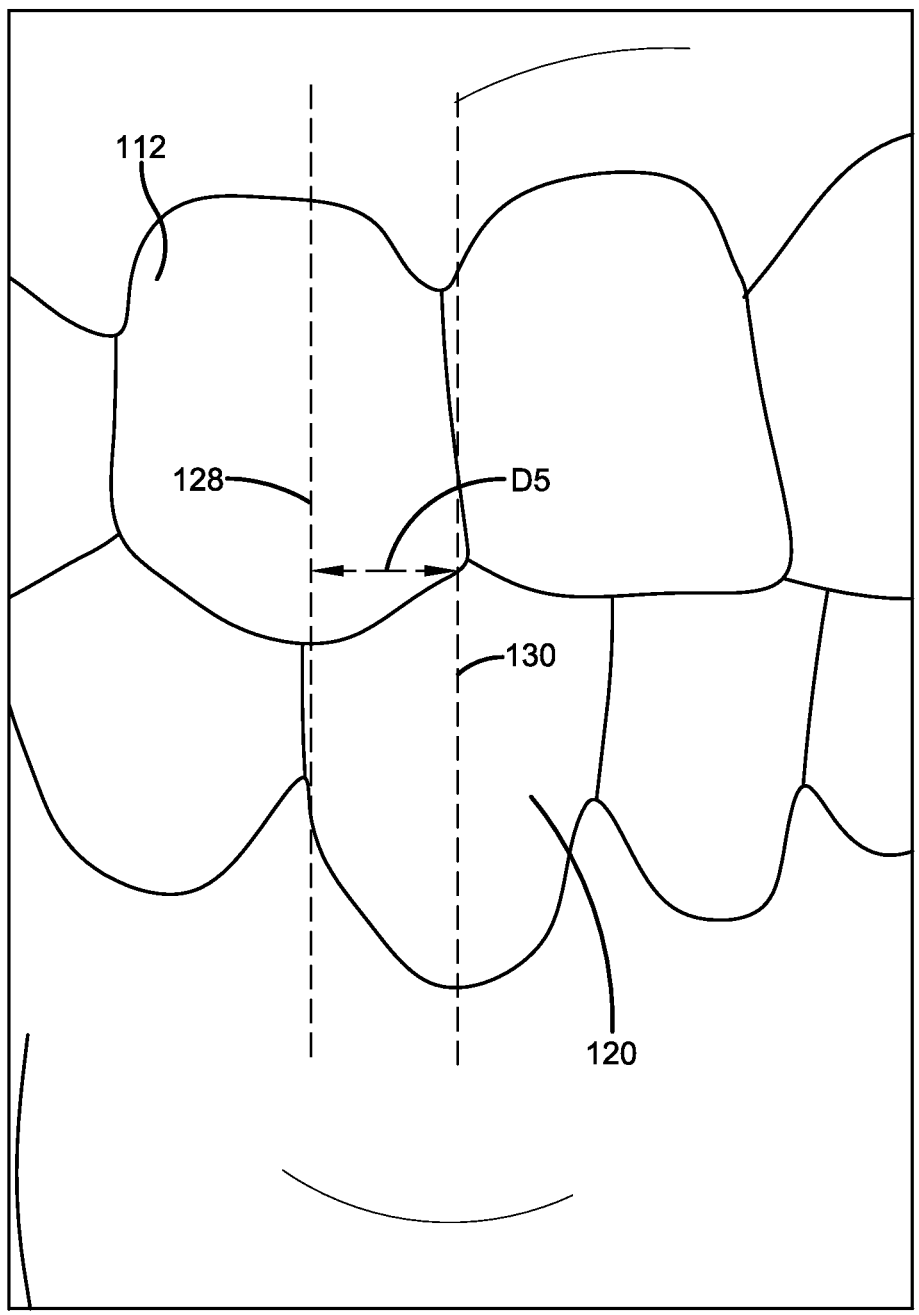
FIG. 16 is a close up view of a portion of the mouth shown in FIG. 15.
Figure 23:
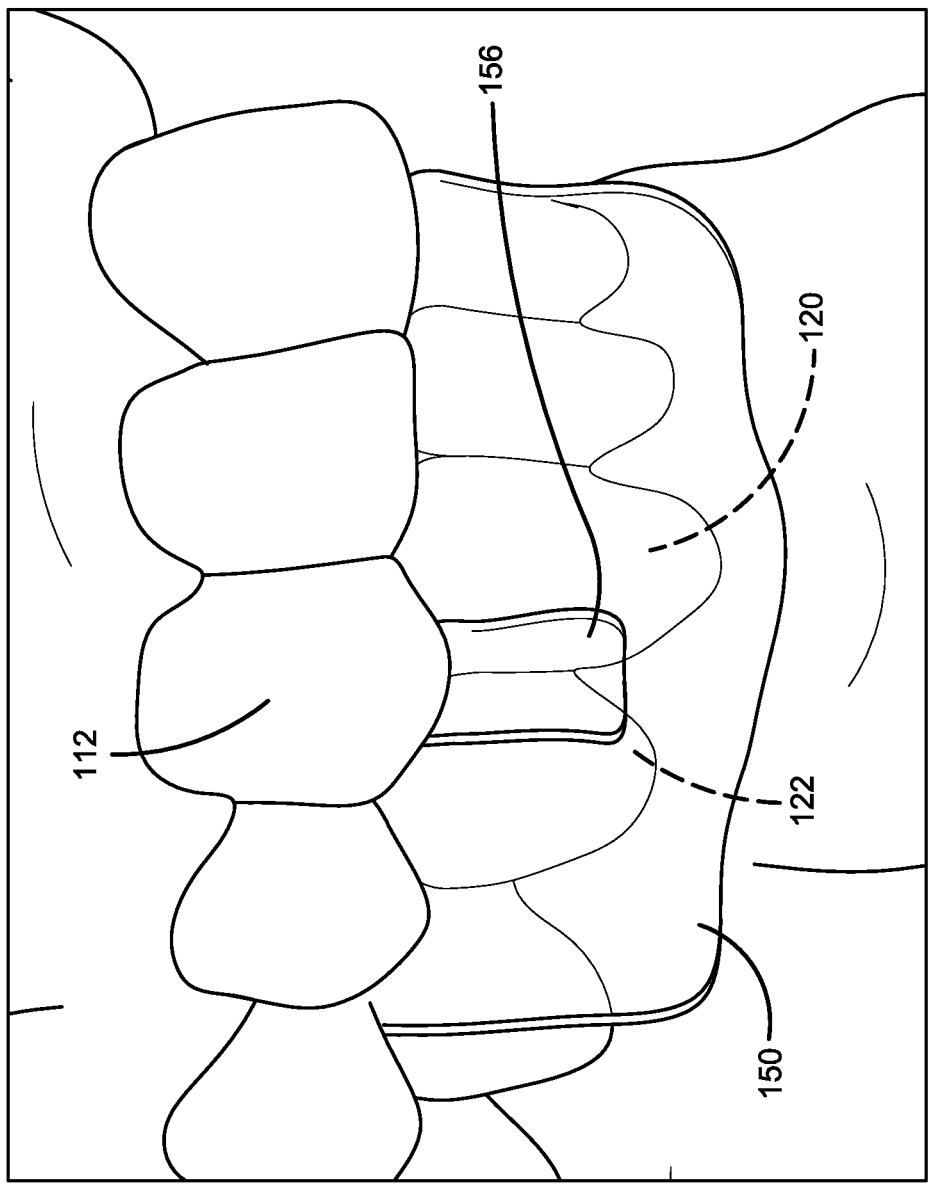
FIG. 23 is a front perspective view of a dental appliance used to treat the patient having the teeth shown in FIG. 16.

FIG. 23 shows one embodiment of use of dental appliance 150 retained on the patient's lower jaw with the teeth shown in FIG. 16. The treatment portion 156 is positioned to be contacted by the upper canine tooth 112, regardless of the position of the patient's lower canine tooth 120. In other embodiments, the dental appliance may be retained to the patient's upper jaw.

The dental appliances disclosed above may also be used as a diagnostic tool. As one example, after the patient has warn the dental appliance for a determinative period of time, the dentist may then inspect the dental appliance to determine the severity of a patient's "bruxing" habits. As another example, after the patient has warn the dental appliance for a determinative period of time, the dentist may then inspect the dental appliance to confirm the size and relative placement of the treatment portions. Such diagnostic use is to be considered "treating the patient" in the patent claims below.

Numerous embodiments have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

I claim:

1. A dental appliance for use with an associated patient having a mouth comprising: (1) a lower jaw comprising lower teeth comprising: (a) lower incisor teeth; (b) a first lower canine tooth; (c) a second lower canine tooth; and, (d) at least one premolar tooth; and, (2) an upper jaw comprising upper teeth comprising: (a) a first upper canine tooth on a first side of the upper jaw; and, (b) a second upper canine tooth on a second side of the upper jaw; the dental appliance comprising:
 a body comprising a front wall, a back wall, and a top connecting the front wall to the back wall, the body defining:
  an incisor reception zone suitable to receive the lower incisor teeth;
  a first canine reception zone suitable to receive the first lower canine tooth;
  a second canine reception zone suitable to receive the second lower canine tooth;
  a first treatment portion that: (1) is positioned on the top of the body; (2) has an upper surface; (3) has a lower surface separated from the upper surface by a first thickness; and, (4) is adapted to be positioned within the mouth with the lower surface in physical contact with at least one of the lower teeth and the upper surface positioned to be physically contacted by the first upper canine tooth when the mouth is in a maximum inter-cuspation position;
  a second treatment portion that: (1) is positioned on the top of the body; (2) has an upper surface; (3) has a lower surface separated from the upper surface by a second thickness; and, (4) is adapted to be positioned within the mouth with the lower surface in physical contact with at least one of the lower teeth and the upper surface positioned to be physically contacted by the second upper canine tooth when the mouth is in a maximum inter-cuspation position;
 wherein:
 (A) other than the first and second treatment portions, the top has a maximum thickness;
 (B) the first thickness and the second thickness are greater than the maximum thickness; and,
 (C) the dental appliance is adapted to be positioned within the mouth with: (1) the upper surface of the first treatment portion positioned to be physically contacted by the first upper canine tooth when the mouth is in a maximum inter-cuspation position; (2) the upper surface of the second treatment portion positioned to be physically contacted by the second upper canine tooth when the mouth is in a maximum inter-cuspation position; and (3) no portion of the dental appliance extending posteriorly beyond the associated patient's at least one premolar tooth.

2. The dental appliance of claim 1 wherein the associated patient's lower jaw comprises first and second lower premolar teeth; the body further defining: a first premolar reception zone adapted to receive the first lower premolar tooth; and, a second premolar reception zone adapted to receive the second lower premolar tooth.

3. The dental appliance of claim 1 wherein the first and second thicknesses are not greater than 1.5 millimeters.

4. The dental appliance of claim 1 wherein the front and back walls are adapted to: completely cover the lower incisor teeth and the first and second lower canine teeth; and, partially cover dental alveolus from which the lower incisor teeth and the first and second lower canine teeth extend.

5. The dental appliance of claim 1 wherein the body is formed of ethylene vinyl acetate.

6. A dental appliance for use with an associated patient having a mouth comprising: (1) a lower jaw comprising lower teeth; and, (2) an upper jaw comprising upper teeth comprising: (a) a first upper canine tooth on a first side of the upper jaw; (b) a second upper canine tooth on a second side of the upper jaw; and, (c) at least one premolar tooth; the dental appliance comprising:
 a first part comprising: (1) a retaining surface; and, (2) a top including a treatment portion having: (a) a first surface; and, (b) a second surface opposite the first surface and separated from the first surface by a first thickness;
 a second part comprising: (1) a retaining surface; (2) a top including a treatment portion having: (a) a first surface; and, (b) a second surface opposite the first surface and separated from the first surface by a second thickness;
 wherein:
 (A) other than the first treatment portion, the top of the first part has a maximum thickness;
 (B) the first thickness is greater than the maximum thickness of the first part;
 (C) other than the second treatment portion, the top of the second part has a maximum thickness;
 (D) the second thickness is greater than the maximum thickness of the second part;
 (E) the dental appliance is adapted to be positioned within the mouth in a treatment position where: (1) the retaining surface of the first part retains the first part to the mouth with the treatment portion of the first part positioned between the first upper canine tooth and the lower teeth; and, (2) the retaining surface of the second part retains the second part to the mouth with the treatment portion of the second part positioned between the second upper canine tooth and the lower teeth;
 (F) when the mouth is in a maximum inter-cuspation position and the dental appliance is in the treatment position, the dental appliance is adapted to engage the teeth as follows: (1) the first upper canine tooth physically contacts the first surface of the first treatment portion; (2) at least one of the lower teeth physically contacts the second surface of the first treatment portion; (3) the second upper canine tooth physically contacts the first surface of the second treatment portion; (4) at least one of the lower teeth physically contacts the second surface of the second treatment portion; and, (5) no upper tooth, other than the first and second upper canine teeth, physically contacts the dental appliance; and,
 (G) when the dental appliance is positioned within the mouth in the treatment position, no portion of the dental appliance extends posteriorly beyond the associated patient's at least one premolar tooth.

7. The dental appliance of claim 6 wherein the first and second parts are formed of ethylene vinyl acetate.

8. The dental appliance of claim 6 wherein:
 the first part comprises a front wall, a back wall and the top of the first part connects the front wall to the back wall;
 the front and back walls of the first part define the retaining surface of the first part;

the second part comprises a front wall, a back wall and the top of the second part connects the front wall to the back wall; and, the front and back walls of the second part define the retaining surface of the second part.

9. The dental appliance of claim 6 wherein the first and second parts are connected.

10. The dental appliance of claim 6 wherein the first and second thicknesses are not greater than 1.5 millimeters.

11. The dental appliance of claim 6 wherein the retaining surface of the first part is adapted to retain the first part to the patient's lower jaw and the retaining surface of the second part is adapted to retain the second part to the patient's lower jaw.

12. The dental appliance of claim 6 wherein the retaining surface of the first part is adapted to retain the first part to the patient's upper jaw and the retaining surface of the second part is adapted to retain the second part to the patient's upper jaw.

\* \* \* \* \*